(12) United States Patent
Kurokawa et al.

(10) Patent No.: US 11,576,740 B2
(45) Date of Patent: Feb. 14, 2023

(54) BENDING STRUCTURE AND FLEXIBLE TUBE FOR MEDICAL MANIPULATOR

(71) Applicant: NHK SPRING CO., LTD., Yokohama (JP)

(72) Inventors: Shimpei Kurokawa, Yokohama (JP); Yuki Hotoda, Yokohama (JP); Shinji Iino, Yokohama (JP)

(73) Assignee: NHK Spring Co., Ltd., Kanagawa (JP)

(*) Notice: Subject to any disclaimer, the term of this patent is extended or adjusted under 35 U.S.C. 154(b) by 272 days.

(21) Appl. No.: 16/755,121

(22) PCT Filed: Oct. 2, 2018

(86) PCT No.: PCT/JP2018/036883
§ 371 (c)(1),
(2) Date: Apr. 9, 2020

(87) PCT Pub. No.: WO2019/073860
PCT Pub. Date: Apr. 18, 2019

(65) Prior Publication Data
US 2020/0323600 A1 Oct. 15, 2020

(30) Foreign Application Priority Data
Oct. 12, 2017 (JP) .............................. JP2017-198854

(51) Int. Cl.
*A61B 34/00* (2016.01)
*A61B 34/30* (2016.01)
(Continued)

(52) U.S. Cl.
CPC .............. *A61B 34/71* (2016.02); *A61B 34/30* (2016.02); *B25J 18/06* (2013.01);
(Continued)

(58) Field of Classification Search
CPC .......... A61B 34/71; A61B 2017/00314; A61B 2017/00323; A61B 34/30;
(Continued)

(56) References Cited

U.S. PATENT DOCUMENTS 5,271,381 A * 12/1993 Ailinger ............... A61B 1/0055
600/128
6,817,974 B2 * 11/2004 Cooper ............ A61B 17/00234
606/205
(Continued)

FOREIGN PATENT DOCUMENTS

JP 2006-508765 A 3/2006
JP 2014-038075 A 2/2014

*Primary Examiner* — George J Ulsh
(74) *Attorney, Agent, or Firm* — Norris McLaughlin, P.A.

(57) ABSTRACT

Provided are a bending structure and a flexible tube for a medical manipulator, which comprise a main body that is composed of the wave washers stacked in an axial direction and kept a stacked state, the main body being bendable according to the expansion and contraction in the axial direction. Accordingly, linearity of load characteristics based on load and a bending angle is made high to make it possible to obtain the flexible tube having superior load bearing and bendability while conducting size reduction.

8 Claims, 22 Drawing Sheets

(51) Int. Cl.
*B25J 18/06* (2006.01)
*A61B 17/00* (2006.01)

(52) U.S. Cl.
CPC .............. *A61B 2017/00314* (2013.01); *A61B 2017/00323* (2013.01); *A61B 2034/301* (2016.02)

(58) Field of Classification Search
CPC ........ A61B 2034/301; A61B 2034/306; A61B 17/29; B25J 18/06
See application file for complete search history.

(56) References Cited

U.S. PATENT DOCUMENTS

| | | | |
|---|---|---|---|
| 8,790,243 B2* | 7/2014 | Cooper | A61B 34/30 600/101 |
| 2004/0138700 A1 | 7/2004 | Cooper et al. | |
| 2008/0051632 A1* | 2/2008 | Ito | A61B 1/0607 600/114 |
| 2016/0235274 A1* | 8/2016 | Graham | A61B 1/0055 |
| 2017/0095300 A1 | 4/2017 | Devengenzo et al. | |

* cited by examiner

BENDING STRUCTURE AND FLEXIBLE TUBE FOR MEDICAL MANIPULATOR

FIELD OF THE INVENTION

The present invention relates to a flexible tube and a bending structure applicable to a bendable part of a medical manipulator such as a surgical robot.

BACKGROUND OF THE INVENTION

In recent medical treatment, a medical manipulator such as robot forceps for a surgical robot and manual forceps becomes broadly widened in order to enable to lighten burdens on both a patient and a doctor at the time of a surgery.

The medical manipulator such as the robot forceps and manual forceps allows a doctor to insert an arm as well as an endoscope camera through a small wound of a patient and perform a surgery with feeling as if forceps are actually manipulated while capturing a surgical field with eyes through a 3D monitor.

As such a medical manipulator, there is one which provides an arm with a joint function by means of a bendable part to secure a high degree of freedom and allow more fine surgical operation like Patent document 1.

In the medical manipulator, a coiled spring is used for the bendable part of the arm so that the coiled spring is bent by drawing drive wires passing through an inside thereof.

The arm of the medical manipulator is desired to be reduced in size in order to make a wound of a patient smaller and lighten mental and physical burdens. Accordingly, the bendable part used in the arm is also desired to be reduced in size.

In the technique of Patent document 1, however, the bendable part is composed of the coiled spring and therefore is limited on the seize reduction for necessity of securing load bearing and bendability.

Such a problem is existed in not only the above-mentioned medical manipulator such as the robot forceps and the manual forceps but also other types of medical manipulators such as an endoscope camera.

PATENT DOCUMENT 1: JP 2014-38075 A

SUMMARY OF THE INVENTION

A problem to be solved is that there is a limit on securing load bearing and bendability while conducting size reduction.

In order to conduct size reduction and provide superior load bearing and bendability, the present invention is most characterized by a flexible tube through which drive wires for a medical manipulator are passed in an axial direction and being configured to be bent according to operation of the drive wires, comprising a main body having wave washers stacked in the axial direction and kept a stacked state, the main body being bendable according to expansion and contraction in the axial direction.

Since the main body is configured by stacking the wave washers so as to be bent according to the expansion and contraction of each wave washer in the axial direction, the present invention makes it possible to obtain the flexible tube having superior load bearing and bendability while conducting size reduction.

BRIEF DESCRIPTION OF THE DRAWINGS

FIGS. 9(A) and 9(B) are sectional views of the flexible tube in which
FIG. 9(A) illustrates a normal state and FIG. 9(B) illustrates a bending state;
FIGS. 23(A) and 23(B) are sectional views of the bending structure in which
FIG. 23(A) illustrates a normal state and FIG. 23(B) illustrates a bending state.

EMBODIMENT FOR CARRYING OUT THE INVENTION

The present invention accomplishes the object of conducting size reduction and providing superior load bearing and bendability by a flexible tube in which wave washers are stacked to form a main body, the flexible tube configured to be bendable according to expansion and contraction of each wave washer in an axial direction.

Each wave washer is provided with crests and troughs in a circumferential direction, the troughs being in interpositions between the crests, and the crests and the troughs of adjacent wave washers are preferably in contact with each other in the wave washers. In this case, keeping a stacked state of the wave washers may be performed by fixing the crests and the troughs of the adjacent wave washers.

Further, the wave washers preferably have insertion holes through which the drive wires are passed. In this case, the keeping of the stacked state of the wave washers may be performed by positioning the adjacent wave washers with the drive wires without fixing the crests and the troughs of the adjacent wave washers.

Further, an elastic member may be provided in the flexible tube to form a bending structure. The elastic member is configured to be arranged in the main body of the flexible tube, have higher rigidity in the axial direction than the main body, and be bendable according to the bending of the main body.

The elastic member may employ a variety of shapes and be, for example, a coiled spring, a solid cylinder, a hollow cylinder or the like located on an axial center portion of the main body.

Figure 1:
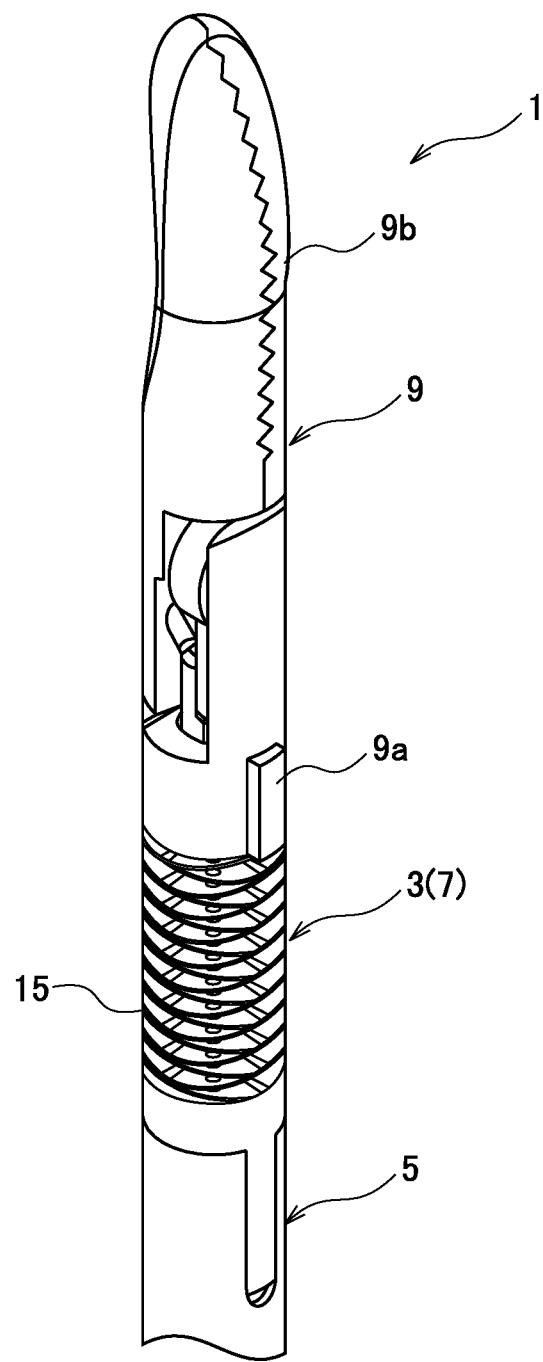
FIG. 1 is a perspective view illustrating robot forceps having a flexible tube according to an embodiment 1 of the present invention.
Figure 2:
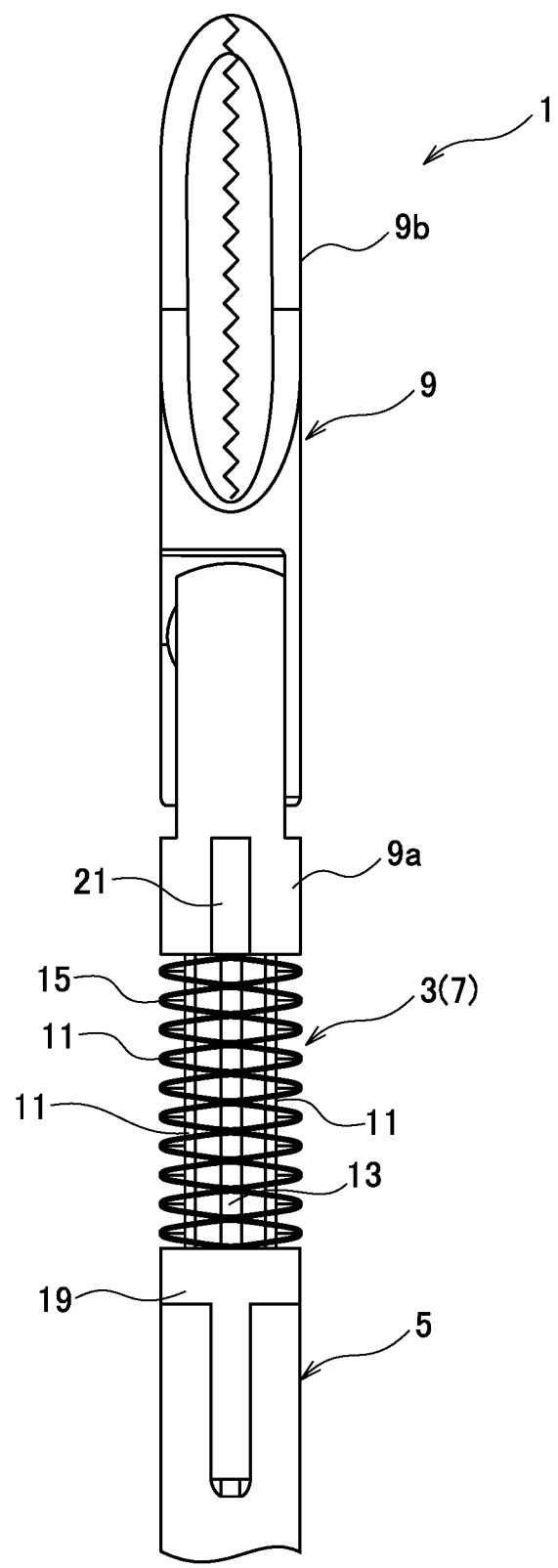
FIG. 2 is a front view of the robot forceps of FIG. 1.
Figure 3:
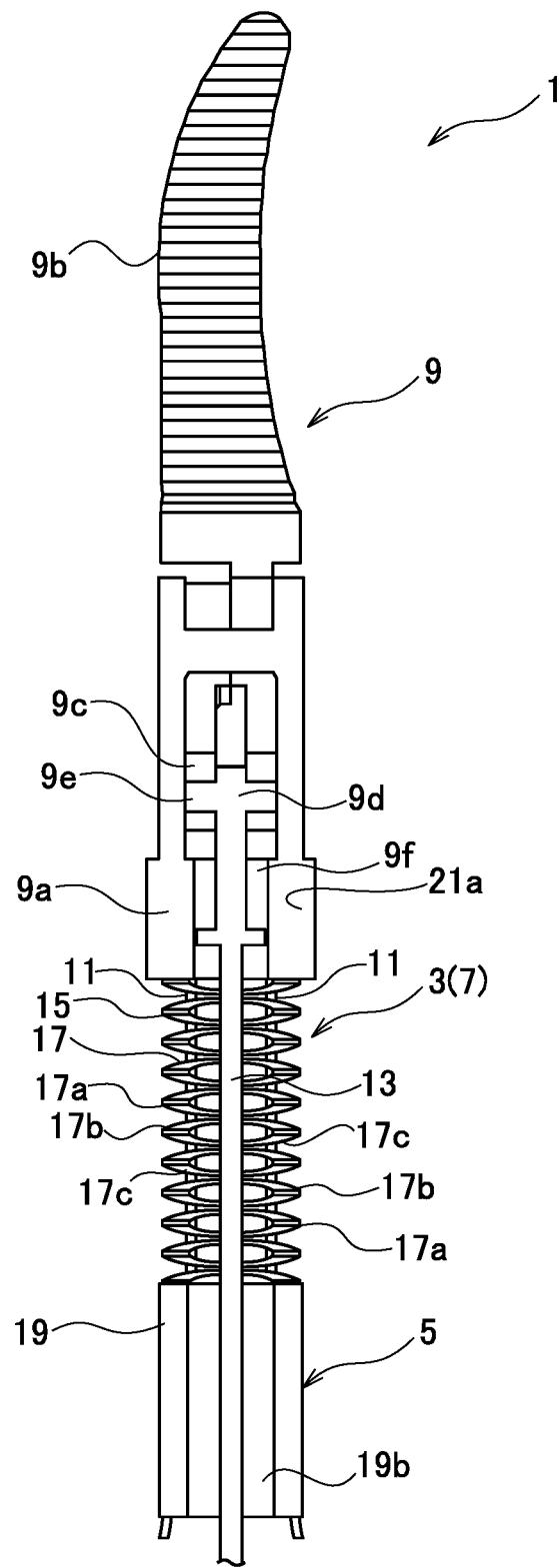
FIG. 3 is a sectional view of the robot forceps of FIG. 1.

FIG. 1 is a perspective view illustrating robot forceps having a flexible tube according to the embodiment 1 of the present invention, FIG. 2 is a front view of the same, and FIG. 3 is a sectional view of the same.

Robot forceps 1 compose a front end of a robot arm of a surgical robot as a medical manipulator. In addition, the robot forceps 1 are an example of a medical manipulator.

It should be noted that a medical manipulator to which the flexible tube 3 is applicable is not limited particularly as long as, regardless of whether being attached to a surgical robot, one is manipulated by a hand of a doctor or the like and has a bendable part which performs bending motion.

The medical manipulator, therefore, also includes an endoscope camera, manual forceps and the like that are not attached to the surgical robot.

The robot forceps 1 of the present embodiment comprises a shaft part 5, a bendable part 7, and a grasping unit 9.

The shaft part 5 is formed into, for example, a cylindrical shape. Inside the shaft part 5, passings are drive wires 11 for driving the bendable part 7 and a push/pull cable 13 for driving the grasping unit 9. At a front end of the shaft part 5, the grasping unit 9 is provided through the bendable part 7.

The driving wires 11 are sufficient to be cord members, and may be, for example, stranded wires, NiTi (Nickel-titanium) solid wires, piano wires, articulated rods, chains, strings, stitches, ropes or the like, but are not limited particularly.

The bendable part 7 comprises a flexible tube 3 according to the present embodiment. The bendable part 7 (flexible tube 3) passes the drive wires 11 and the push/pull cable 13 therethrough in an axial direction and is bendable according to operation of the driving wires 11. The axial direction means a direction along an axial center of the flexible tube 3, is not necessarily a direction being strictly parallel to the axial center, but also includes a direction slightly inclining relatively to the axial center.

In addition, the push/pull cable 13 is provided on an axial center portion of the bendable part 7 (flexible tube 3). The four driving wires 11 are provided so as to be located at 90 degrees in a circumferential direction according to the present embodiment, and are outwardly displaced and located relatively to the push/pull cable 13 in a radial direction, respectively. The details of the flexible tube 3 will be explained later. In addition, the radial direction is a radial direction of the flexible tube 3.

The grasping unit 9 has a pair of grasping parts 9b which are openably pivotally supported with a base part 9a attached to a front end of the bendable part 7. To the base part 9a, the drive wires 11 passing through the bendable part 7 are connected.

The grasping unit 9, therefore, is capable of orienting the grasping parts 9b to a desired direction while bending the bendable part 7 by operation of the driving wires 11.

To the grasping parts 9b, groove portions 9c are provided so as to be inclined relatively to the axial direction in a closed state of the grasping parts. Projections 9e of a movable piece 9d slidably engage with the groove portions 9c of the grasping parts 9b. The movable piece 9d is arranged in a through-hole 9f of the base part 9a of the grasping unit 9 movably in the axial direction and is connected to the push/pull cable 13 passing through the bendable part 7.

The grasping parts 9b, therefore, are configured to be opened and closed by the movable piece 9d moving in the axial direction according to reciprocating movement (push/pull movement) of the push/pull cable 13. It should be noted that the driving of the grasping unit 9 to open and close the grasping parts 9b is not limited to use of the push/pull cable 13 and may be used an air tube or drive cables.

Figure 4:
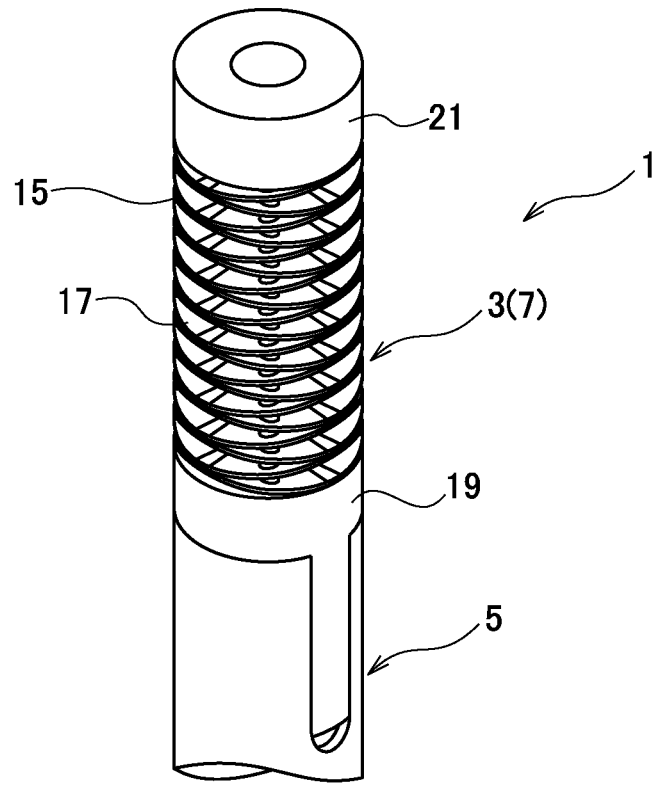
FIG. 4 is a perspective view of the partly omitted robot forceps of FIG. 1.
Figure 5:
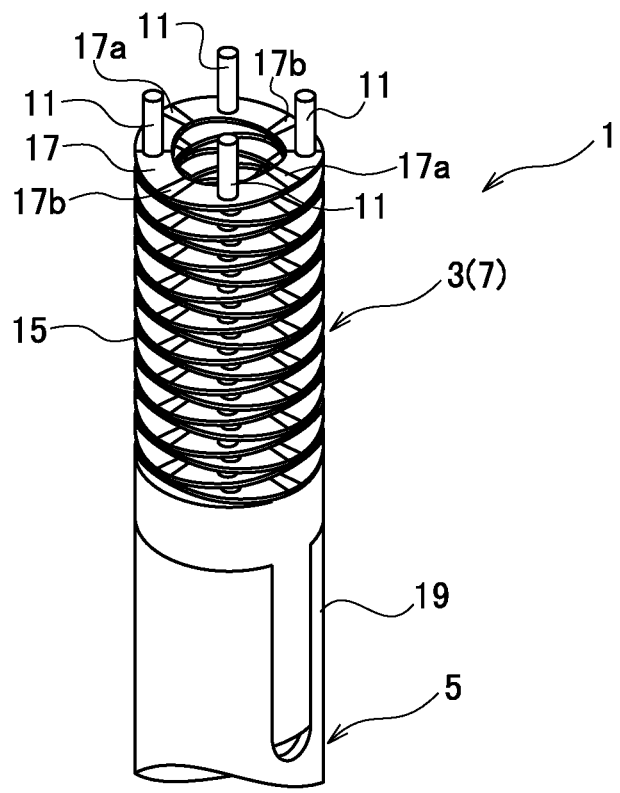
FIG. 5 is a perspective view of the further partly omitted robot forceps of FIG. 4.
Figure 6:
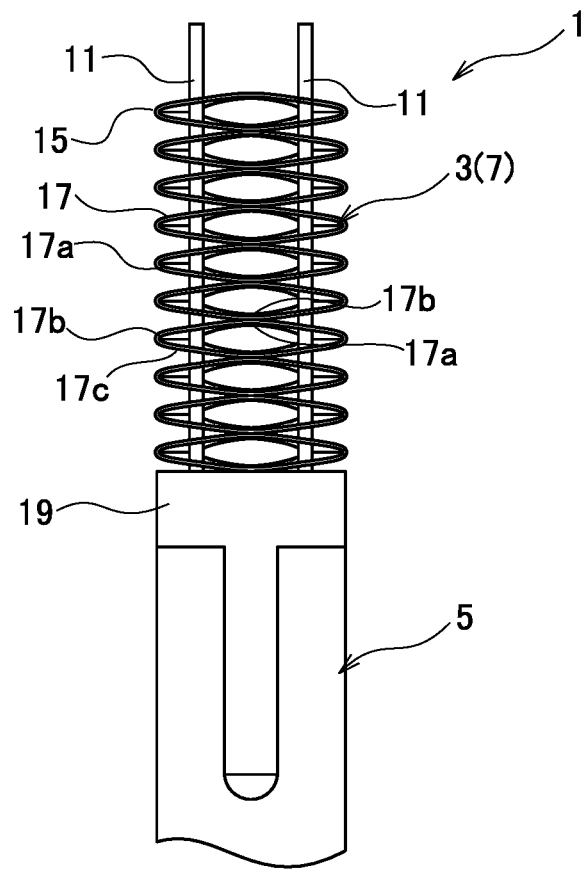
FIG. 6 is a side view of the robot forceps of FIG. 5.
Figure 7:
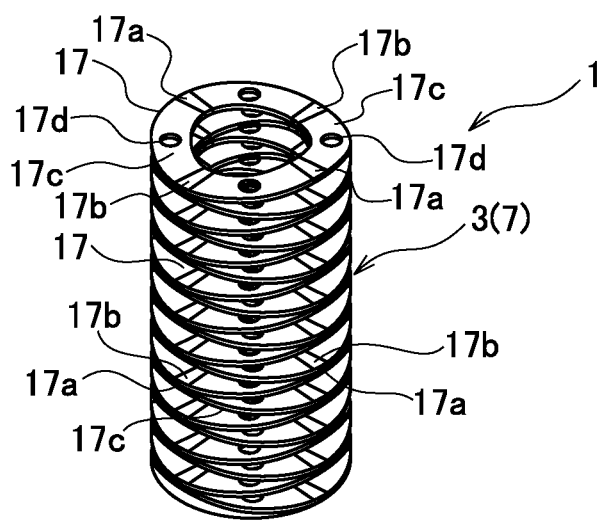
FIG. 7 is a perspective view illustrating the flexible tube of the robot forceps of FIG. 4.
Figure 8A:
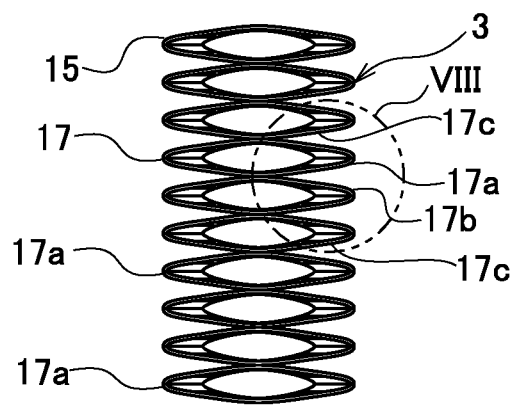
FIG. 8(A) is a side view illustrating the flexible tube of FIG. 4
Figure 8B:
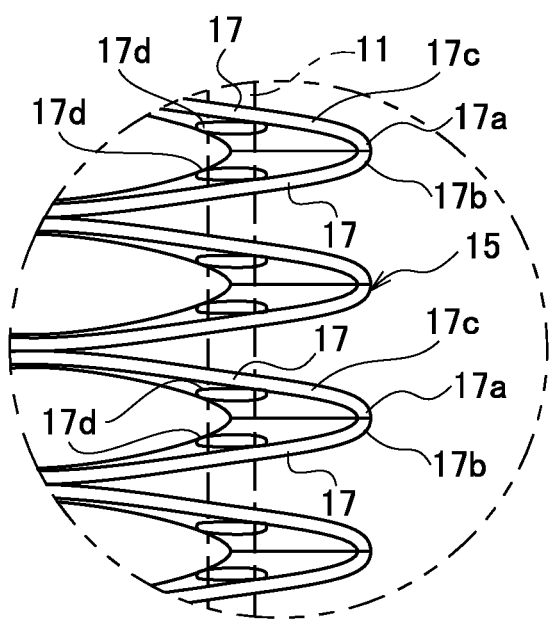
FIG. 8(B) is an enlarged view of a VIII part of FIG. 8(A)
Figure 9A:
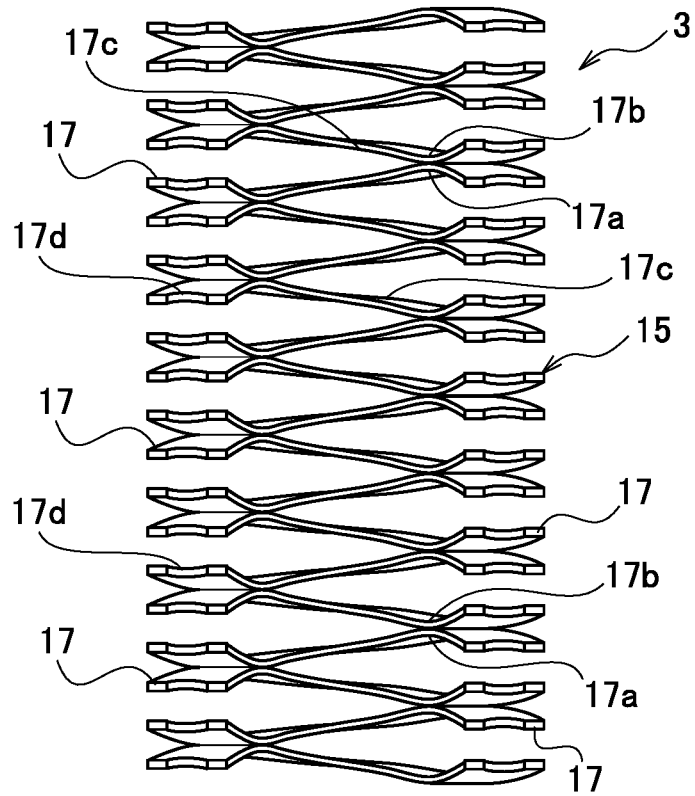

FIG. 4 is a perspective view of the partly omitted robot forceps 1 of FIG. 1. FIG. 5 is a perspective view of the further partly omitted robot forceps of FIG. 4, FIG. 6 is a side view of the same, FIG. 7 is a perspective view illustrating the flexible tube 3, and FIG. 8(A) is a side view of the same and FIG. 8(B) is an enlarged view of a VIII part of FIG. 8(A). FIG. 9 is a set of sectional views illustrating the flexible tube 3 in which FIG. 9(A) illustrates a normal state and (B) illustrates a bending state. In addition, FIG. 8 is a state when viewing FIG. 7 from a direction of 45 degrees (right oblique lower of FIG. 7), and FIG. 9 illustrates a sectional plane passing through insertion holes 17d positioned in a right and left direction of FIG. 7 in a state when viewing FIG. 7 from the front in a depth direction.

As illustrated in FIGS. 1-9, the flexible tube 3 resiliently supports the grasping unit 9 relatively to the shaft part 5 as the bendable part 7 of the robot forceps 1. The flexible tube 3 according to the present embodiment is configured by a main body 15 to which the insertion holes 17d are formed.

The main body 15 is formed by stacking wave washers 17 in the axial direction and is bendable according to expansion and contraction of each wave washer 17 in the axial direction.

Each wave washer 17 is formed of metal, ceramics or the like into an annular shape. The wave washer 17 according to the present embodiment is made of stainless steel into a circular annular shape and has a width between inner and outer peripheries in the radial direction being constant. It should be noted that the shape, material and the like of the wave washer 17 may be changed according to required characteristics and the like for the flexible tube 3.

Each wave washer 17 has crests 17a in the circumferential direction and troughs 17b in interpositions between the adjacent crests 17a. The wave washer 17 of the present embodiment has two crests 17a opposing each other in the radial direction and two troughs 17b opposing each other in the radial direction in the interpositions of the crests 17a.

The present embodiment, therefore, alternately provides the crests 17a and the troughs 17b at 90 degrees in the circumferential direction.

It should be noted that the number of the crests 17a and the troughs 17b may be appropriately changed according to required characteristics and the like of the flexible tube 3.

The crests 17a and the troughs 17b are curved in an arc in reverse in the axial direction and are provided so as to span from the outer periphery to the inner periphery of the wave washer 17. Between the wave washers 17 being adjacent to each other in the axial direction, the crests 17a of one wave washer 17 are in contact with the troughs 17b of the other wave washer 17. According to expansion and contraction of the crests 17a and the troughs 17b, each wave washer 17 is resiliently expandable and contractable in the axial direction.

The crests 17a and the troughs 17b being in contact are fixed by an appropriate means such as welding or adhering. Accordingly, the main body 15 of the flexible tube 3 is kept the stacked state.

It should be noted that, even if the crests 17a and the troughs 17b being in contact are not fixed to each other, the stacked state of the wave washers 17 may be kept by passing the drive wires 11 through the insertion holes 17d which are explained later.

In addition, the crests 17a and the troughs 17b may not be in contact with each other and may be configured to be slightly deviated from each other in the circumferential direction and be in contact with inclined portions 17c, for example.

In each wave washer 17, intervals between the crests 17a and the troughs 17b are continued by the inclined portions 17c. The inclined portions 17c have a shape being inclined with respect to the radial direction and being slightly twisted between the inner periphery and the outer periphery. To the inclined portions 17c, the insertions holes 17d are formed as the through portions. It should be noted that radii of curvatures of the crests 17a and the troughs 17b, an inclining angle of the inclined portions 17c and the like may be appropriately altered according to required characteristics and the like for the flexible tube 3.

The insertion holes 17d are provided on the respective inclined portions 17c in the circumferential direction of the main body 15. According to the present embodiment, the four drive wires 11 are provided at 90 degrees in the circumferential direction, and accordingly the four insertion holes 17d are provided on the respective inclined portions 17c at 90 degrees in the circumferential direction. The number of the insertion holes 17d may be, however, altered according to the number of the drive wires 11.

Between the inclined portions 17c of the axially adjacent wave washers 17, the insertion holes 17d are communicated with each other in the axial direction and the drive wires 11 are passed through the communicating insertion holes 17d. By the passing, the flexible tube 3 passes the drive wires 11 therethrough in the axial direction as the through portions and functions as a guide to retain the drive wires at given positions.

It should be noted that the through portions may be cutouts or recessed portions radially recessed from an inner periphery or outer periphery of the main body 15 of the flexible tube 3 instead of the insertion holes 17d. The flexible tube 3 may, therefore, axially pass the drive wires 11 alongside the through portions being the recessed portions or the like on the inner periphery or outer periphery.

Further, each insertion hole 17d is located in the middle of the width of the wave washer 17 in the radial direction. The insertion hole 17d may be, however, displaced radially inwardly or outwardly with respect to the middle of the width in the radial direction. Further, radial distances from the axial center of the main body 15 to the respective insertion holes 17d may be appropriately set according to the characteristics of the flexible tube 3 and, for example, may or may not be constant.

A shape of the insertion hole 17d is approximately circular and has the larger diameter than the drive wire 11. The difference in the diameters permits the inclination and displacement of the inclined portions 17c. It should be noted that the shape of the insertion hole 17d is not limited to the circular shape and may be another shape such as rectangular shape.

The main body 15 is provided between first and second connection parts 19, 21. The first and second connections parts 19, 21 respectively composes parts of the front end of the shaft part 5 and the base part 9a of the grasping unit 9 of the robot forceps 1 and are formed of resin, metal or the like into a cylindrical shape.

In the first connection part 19, the driving wires 11 pass through through-holes (not illustrated) in the axial direction. In the second connection part 21, front end portions of the driving wires 11 are fixed into fixing holes (not illustrated). Further, on an axial center portion of the first connection part 19, a cable passing hole 19b is provided to pass the push/pull cable 13 therethrough.

In the flexible tube 3 as the bendable part 7, the movable side located on the grasping unit 9 side bends relatively to the stationary side located on the shaft part 5 side by drawing any one of the drive wires 11 when a doctor manipulates the robot forceps 1. Then, a number of the drive wires 11 are combined to be drawn, thereby to allow the flexible tube to bend omnidirectionally at 360 degrees.

Figure 9B:
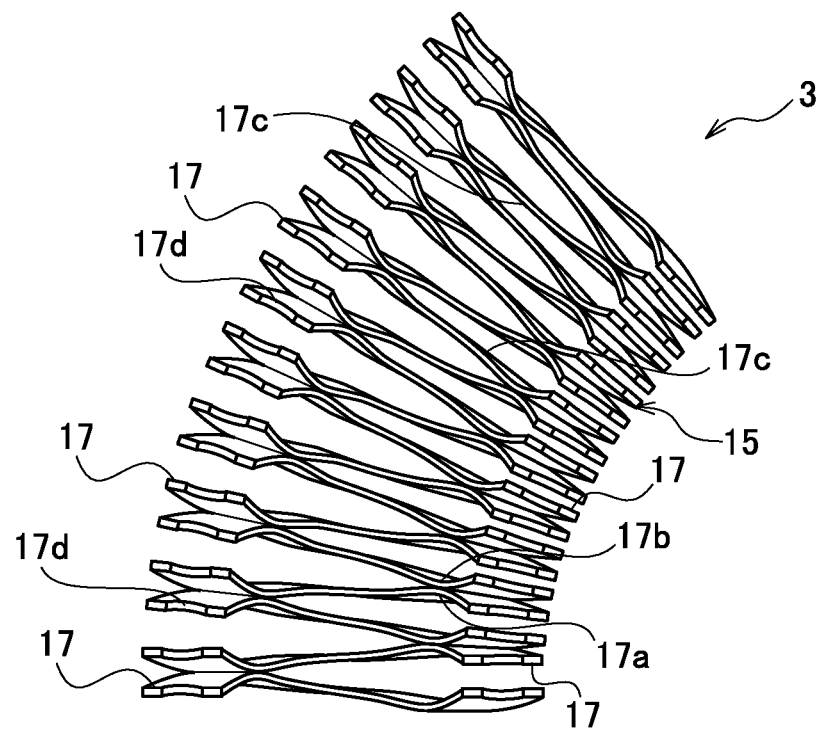

When drawing any one of the drive wires 11 to conduct the bending, the flexible tube 3, as illustrated in FIG. 9(B), is compressed at the crests 17a and the troughs 17b on an inner portion of the bending relative to a neutral axis and is extended at the crests 17a and the troughs 17b on an outer portion of the bending relative to the neutral axis. By deforming in this way, the inclined portions 17c through which the operated drive wire 11 passes get close to each other so that the flexible tube 3 is bent as a whole.

Further, at the time of the bending, the flexible tube 3 passes the drive wires 11 through the insertion holes 17d to retain the drive wires at the appropriate positions, so that the flexible tube 3 stably and accurately conducts the bending motion according to the manipulation of the doctor.

Figure 10:
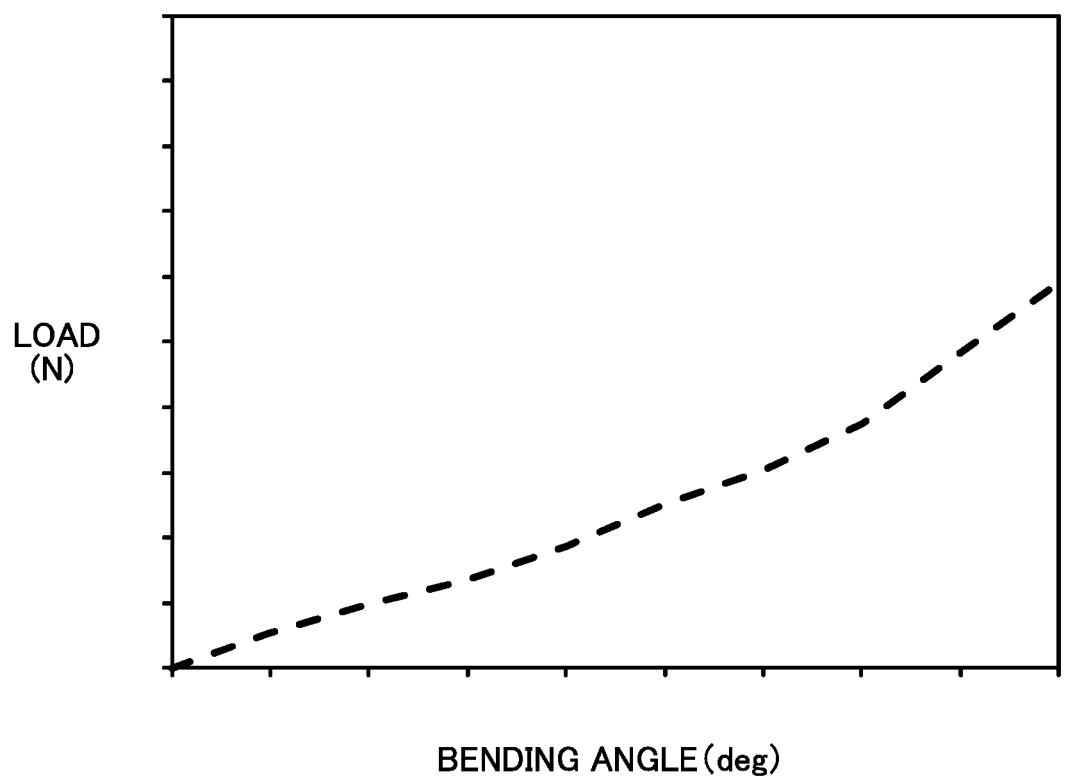
FIG. 10 is a graph illustrating a relationship between loads and bending angles of the flexible tube.

FIG. 10 is a graph illustrating a relationship between loads and bending angles of the flexible tube 3 according to the embodiment 1.

In FIG. 10, loads are plotted when the flexible tube 3 is bent from 0 degree to 90 degrees in a bending angle.

As illustrated in FIG. 10, in the load characteristics based on the load and the bending angle, the linearity of the increase in load relative to the increase from 0 degree to 90 degrees in the bending angle is made high.

The flexible tube 3 of the present embodiment, therefore, provides the superior load bearing and the bendability.

As mentioned above, the flexible tube 3 of the present embodiment comprises the main body 15 that is composed of the wave washers 17 stacked in the axial direction and kept a stacked state, the main body being bendable according to the expansion and contraction in the axial direction.

Accordingly, the present embodiment heightens the linearity of the load characteristics based on the load and the bending angle and makes it possible to obtain the flexible tube 3 having the superior load bearing and bendability while conducting size reduction.

As a result, the flexible tube 3 conducts the stable and accurate bending motion according to the operation of the doctor.

Each wave washer 17 is provided with the crests 17a and the troughs 17b in the circumferential direction, the troughs being in interpositions between the crests, and the crests 17a and the troughs 17b of the adjacent wave washers 17 are in contact with each other in the wave washers 17.

The flexible tube 3 of the present embodiment, therefore, surely conducts the bending motion according to the expansion and contraction of the crests 17a and the troughs 17b.

Further, the present embodiment fixes the crests 17a and the troughs 17b being in contact to each other in the adjacent wave washers 17, and therefore surely keeps the stacked state of the wave washers 17 in which the crests 17a and the troughs 17b are in contact with each other, thereby to more surely conduct the bending motion of the flexible tube 3.

Additionally, the present embodiment fixes the contacting crests 17a and troughs 17b, thereby to provide superior torsional rigidity.

Further, in the present invention, since the wave washers 17 have the insertion holes 17d through which the drive wires 11 are passed, the main body 15 is used as the guide for the drive wires 11 to retain the drive wires 11 at the appropriate positions and conducts the more stable and accurate bending motion.

Figure 11:
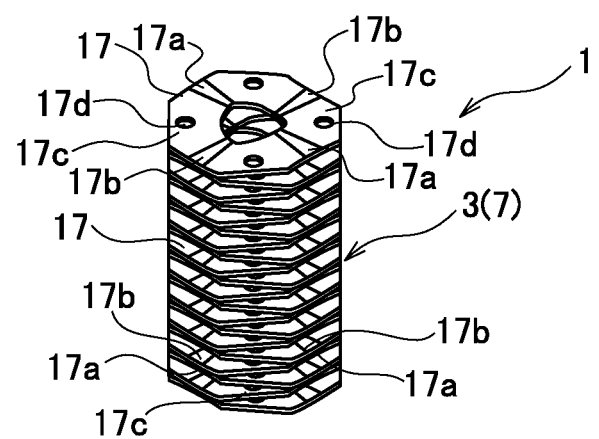
FIG. 11 is a perspective view of a flexible tube according to an embodiment 2 of the present invention.
Figure 12:
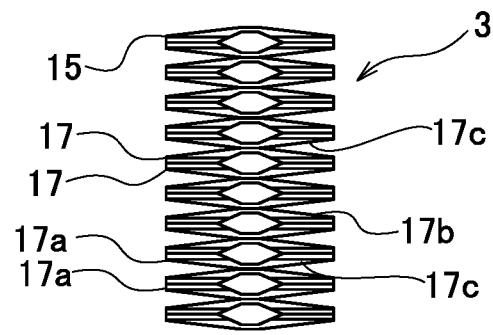
FIG. 12 is a side view of the flexible tube of FIG. 11.
Figure 13:
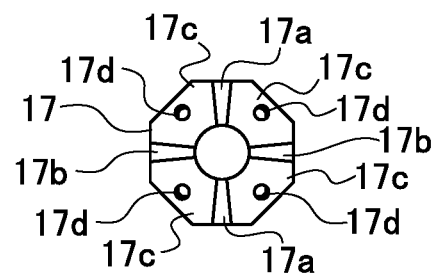
FIG. 13 is a plan view of the flexible tube of FIG. 11.

FIG. 11 is a perspective view illustrating a flexible tube according to the embodiment 2 of the present invention, FIG. 12 is a side view of the same, and FIG. 13 is a plan view of the same. In addition, components in the embodiment 2 corresponding to those in the embodiment 1 are represented with the same numerals to eliminate duplicate explanation.

In the flexible tube 3 according to the present embodiment, a planar shape of wave washers 17 of a main body 15 is altered with respect to the embodiment 1. The others are the same shapes as the embodiment 1.

Each wave washer 17 of the main body 15 has an outer periphery formed into a regular octagon. Crests 17a and troughs 17b are respectively provided to span from middle portions of corresponding sides on the regular octagon to an inner periphery. A shape of the inner periphery of the wave washer 17 is circular similar to the embodiment 1.

Figure 14:
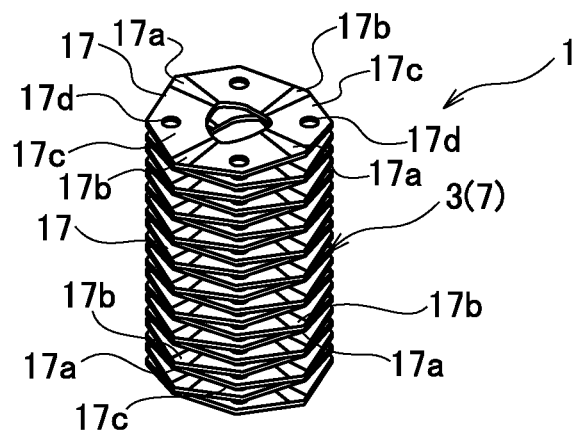
FIG. 14 is a perspective view of a flexible tube according to a modification of the embodiment 2.
Figure 15:
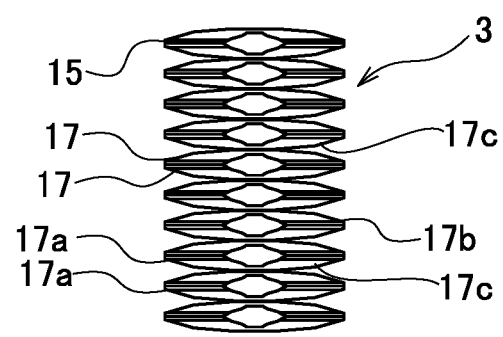
FIG. 15 is a side view of the flexible tube of FIG. 14.
Figure 16:
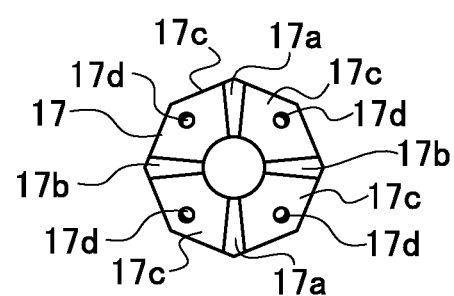
FIG. 16 is a plan view of the flexible tube of FIG. 14.

FIG. 14 is a perspective view of a flexible tube 3 according to a modification, FIG. 15 is a side view of the same, FIG. 16 is a plan view of the same.

The flexible tube 3 of the modification also has an outer periphery of each wave washer 17 of a main body 15 formed into a regular octagon. Crests 17a and troughs 17b, however, are respectively provided to span from corresponding corners on the regular octagon to an inner periphery.

The present embodiment and the modification provide the same effects as the embodiment 1.

Figure 17:
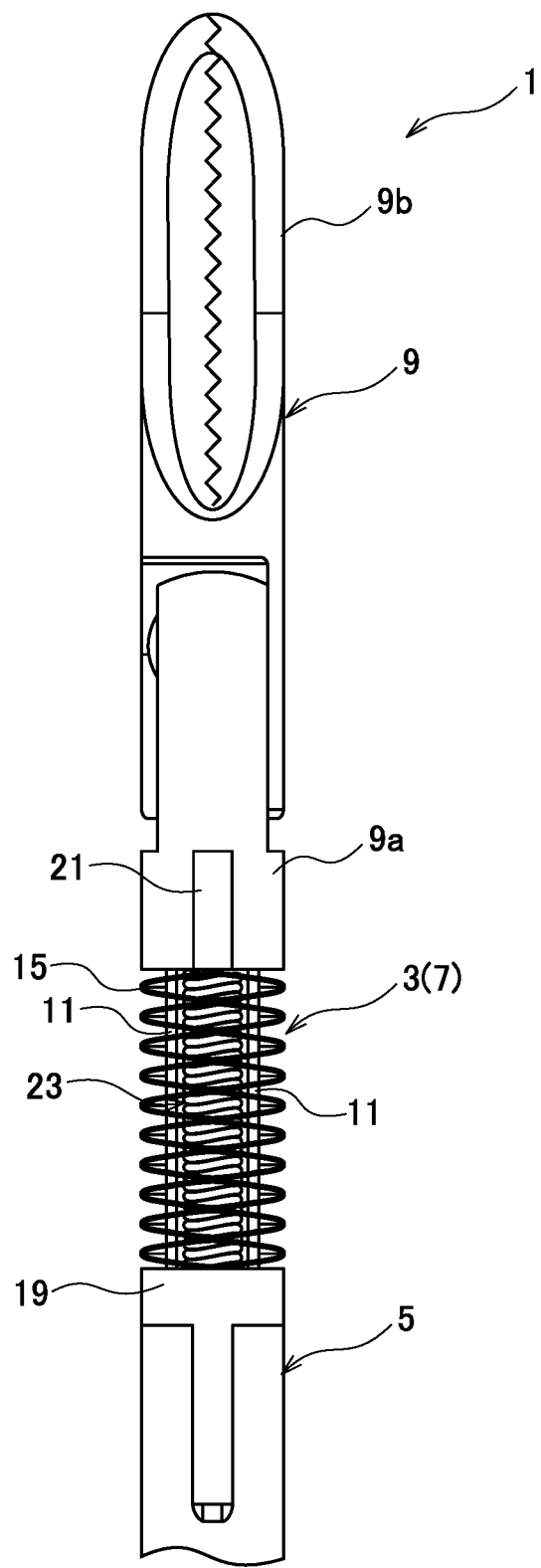
FIG. 17 is a front view of robot forceps that uses a bending structure having a flexible tube according to an embodiment 3 of the present invention.
Figure 18:
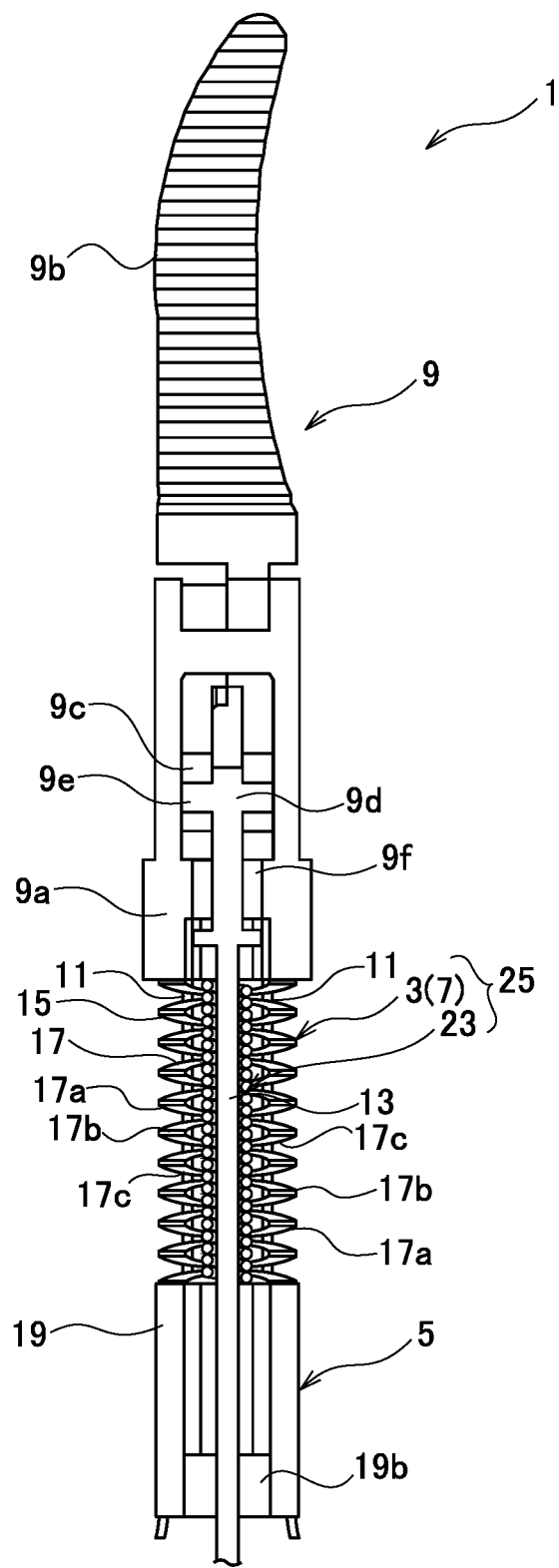
FIG. 18 is a sectional view of the robot forceps of FIG. 17.
Figure 19:
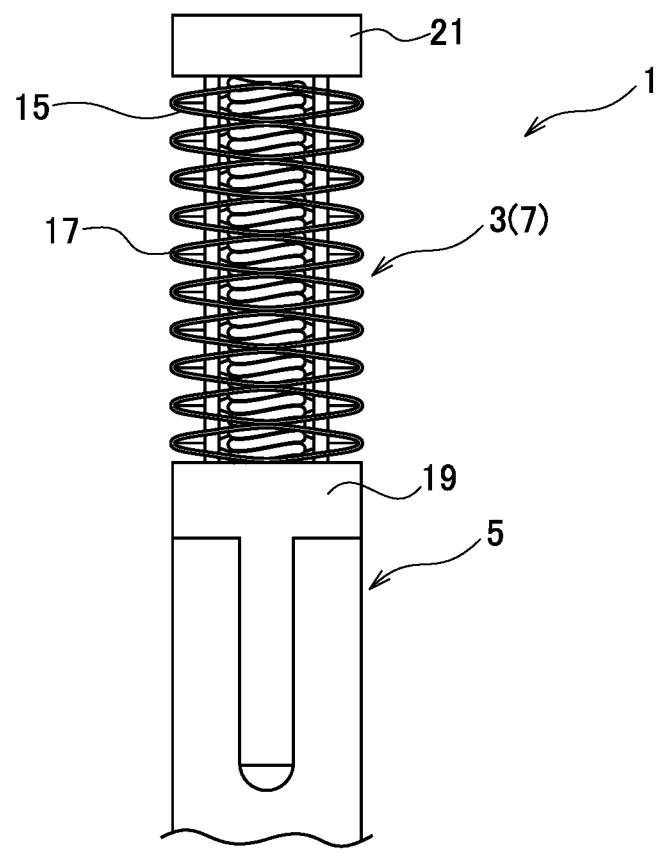
FIG. 19 is a side view of the partly omitted robot forceps of FIG. 17.
Figure 20:
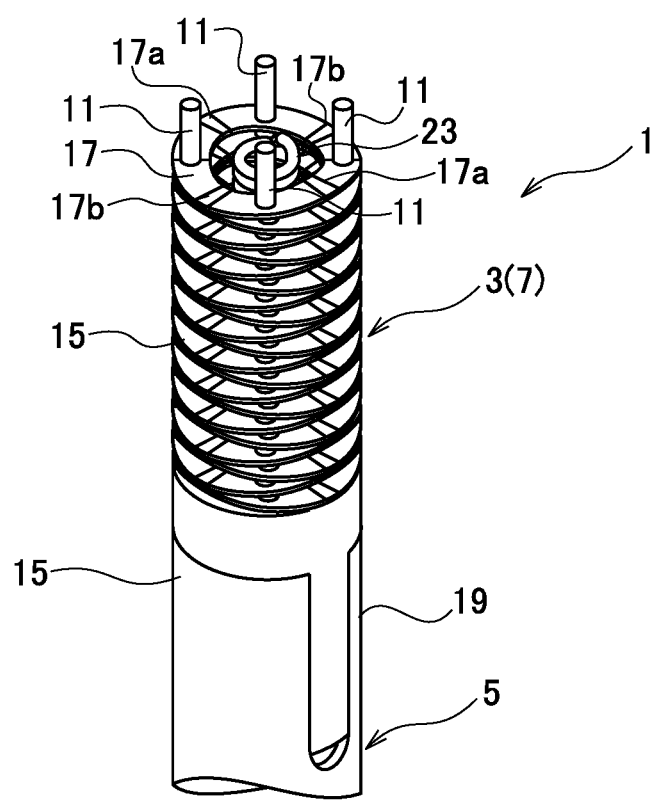
FIG. 20 is a perspective view of the further partly omitted robot forceps of FIG. 19.
Figure 21:
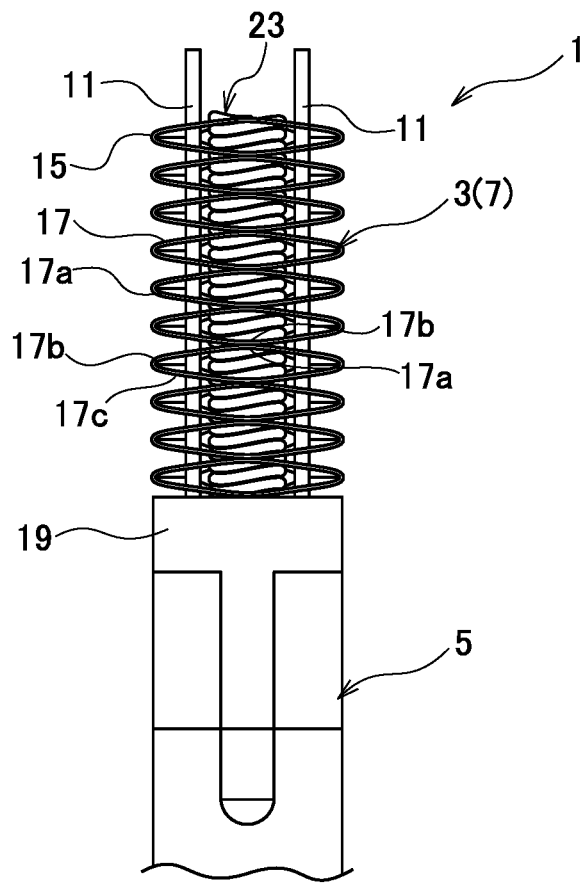
FIG. 21 is a side view of the robot forceps of FIG. 20.
Figure 22:
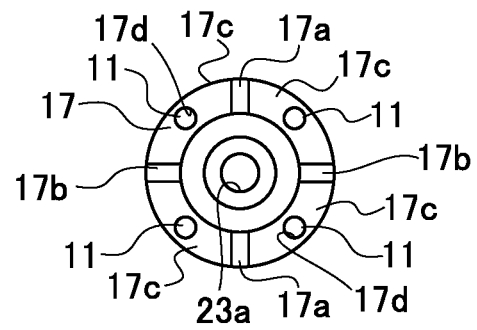
FIG. 22 is a plan view of the robot forceps of FIG. 21.
Figure 23A:
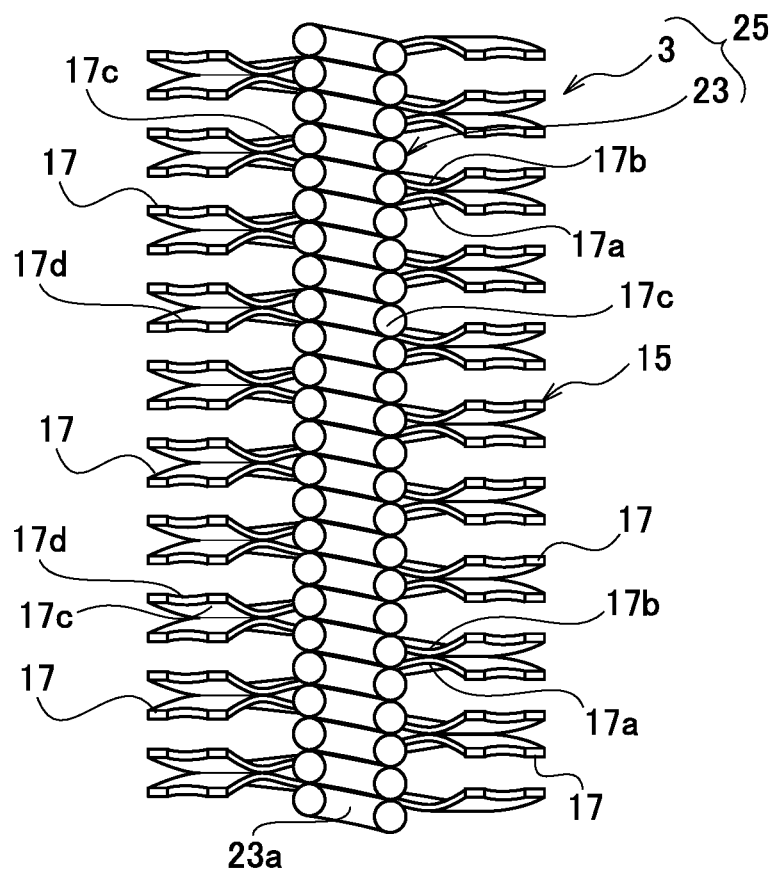
Figure 23B:
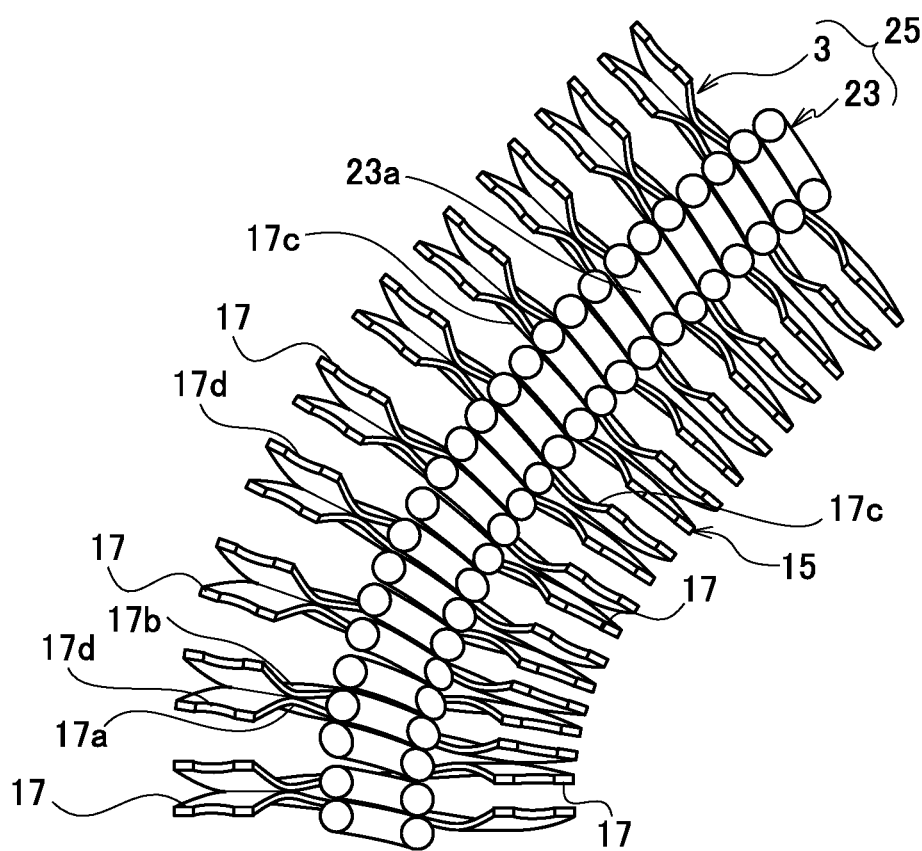

FIG. 17 is a front view illustrating robot forceps that uses a bending structure having a flexible tube according to the embodiment 3 of the present invention, and FIG. 18 is a sectional view of the same, FIG. 19 is a side view of the partly omitted robot forceps of FIG. 17, FIG. 20 is a perspective view of the further partly omitted robot forceps, FIG. 21 is a side view of the same, and FIG. 22 is a plan view of the same. FIG. 23 is a set of sectional views of the bending structure in which FIG. 23(A) illustrates a normal state and FIG. 23(B) illustrates a bending state. In addition, components in the embodiment 3 corresponding to those in the embodiment 1 are represented with the same numerals to eliminate duplicate explanation.

According to the present embodiment, an elastic member 23 is arranged in the flexible tube 3 of the embodiment 1 to form a bending structure 25.

The elastic member 23 is a coiled spring made of metal, in particular a close contact coiled spring. In addition, the close contact coiled spring means a coiled spring in which coils are in closely contact with each other in a free state. As the elastic member 23, a non-close contact coiled spring may be used, the non-close contact coiled spring having a gap between coils in a free state.

The elastic member 23 of the present embodiment has a sectional shape of an element wire of the coiled spring being circular. The sectional shape of the element wire of the coiled spring may be, however, another shape such as rectangular or oval shape.

The elastic member 23 is arranged on the axial center portion of the flexible tube 3 so as to define a cable insertion hole 23a through which a push/pull cable 13 passes on an inner periphery. An outer periphery of the elastic member 23 has a gap with respect to an inner periphery of the flexible tube 3.

In an axial direction, the elastic member 23 extends over at least a whole main body 15 of the flexible tube 3, rigidity against compression of which is set higher than that of the flexible tube 3. Accordingly, the elastic member 23 is capable of preventing the flexible tube 3 from being unexpectedly compressed in the axial direction.

Further, the elastic member 23 is bendable according to the flexible tube 3 and has a function to adjust load characteristics of the flexible tube 3 according to load characteristics in a bending direction.

Figure 24:
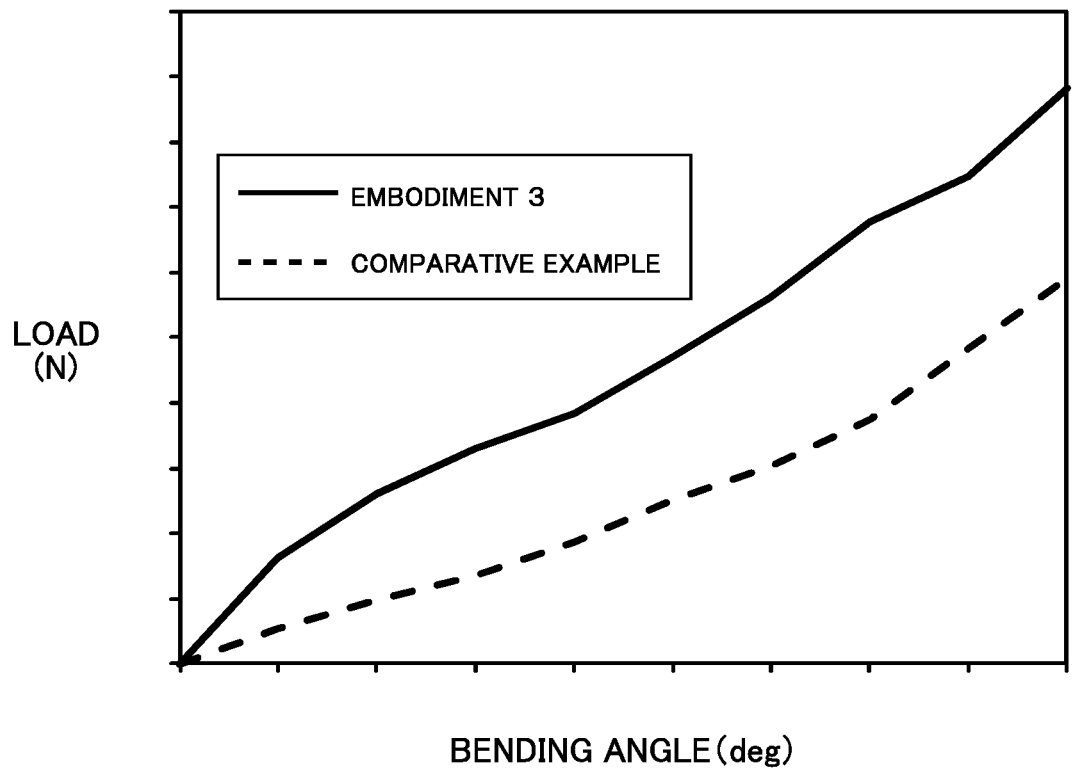
FIG. 24 is a graph illustrating relationships between loads and bending angles of bending structures.

FIG. 24 is a graph illustrating relationships between loads and bending angles of the bending structures 25 according to the embodiment 3 and a comparative example.

As the comparative example, the relationship between the loads and the bending angles of the flexible tube 3 of the embodiment 1 is illustrated. The embodiment 3, similar to the embodiment 1, loads are plotted when the bending structure 25 is bent from 0 degree to 90 degrees in the bending angle and thereafter returns back to 0 degree.

As illustrated in FIG. 24, the embodiment 3 have high linearity, so that load bearing and bendability are superior.

As mentioned above, the bending structure 25 of the present embodiment is provided with the elastic member 23 being arranged in the main body 15 of the flexible tube 3, having the higher rigidity in the axial direction than the main body 15, and being bendable according to the bending of the flexible tube 3.

The bending structure 25 of the present embodiment is, therefore, capable of preventing the flexible tube 23 from being unexpectedly compressed.

Accordingly, although behavior of the bendable part 7 according to operation of driving wires 11 may be unstable if the flexible tube 3 is unexpectedly compressed, the present embodiment suppresses such unstable behavior. Further, a path length is not varied at the time of the bending, so that operation of the grasping unit 9 is stable.

Further, the bending structure 25 of the present embodiment adjusts the load characteristics of the flexible tube 3 according to the load characteristics in the bending direction of the elastic member 23.

In addition, the present embodiment provides the same effects as the embodiment 1.

It should be noted that the elastic member 23 is applicable to the embodiment 2.

Figure 25:
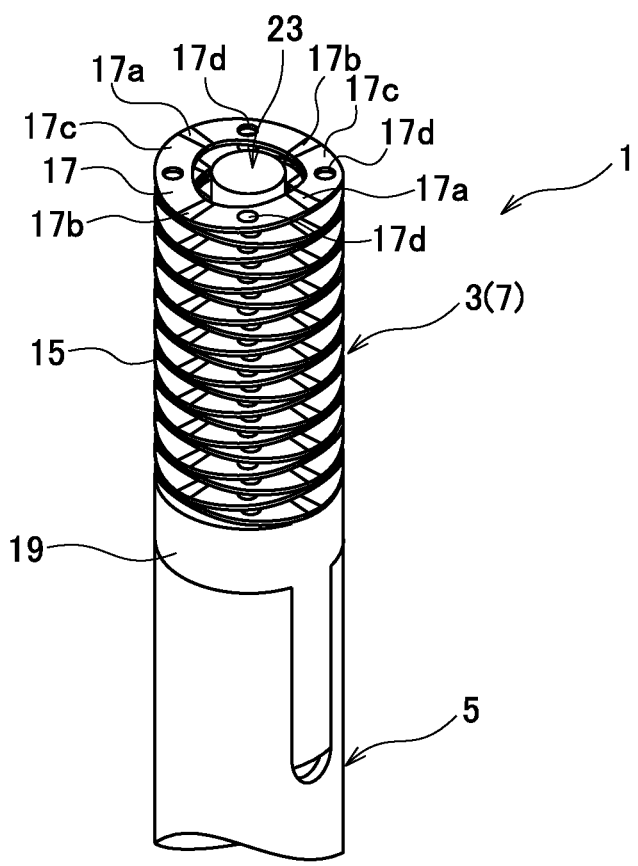
FIG. 25 is a perspective view of partly omitted robot forceps using a bending structure according to an embodiment 4 of the present invention.
Figure 26:
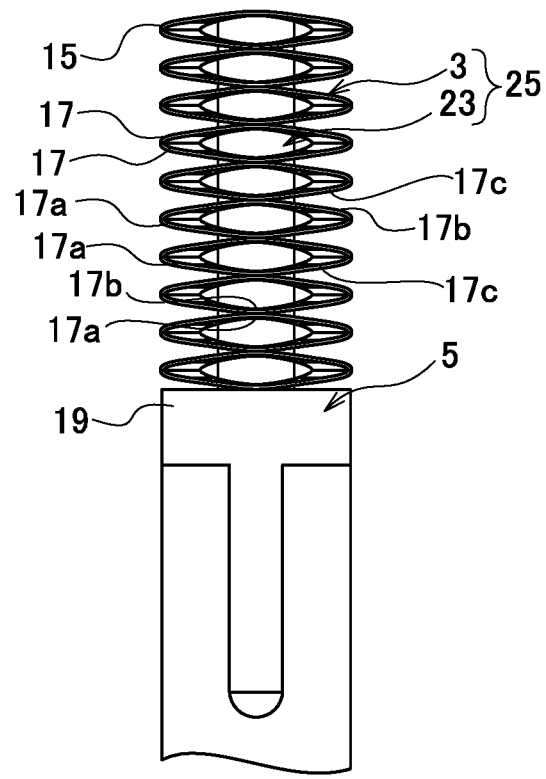
FIG. 26 is a side view of the robot forceps of FIG. 25.
Figure 27:
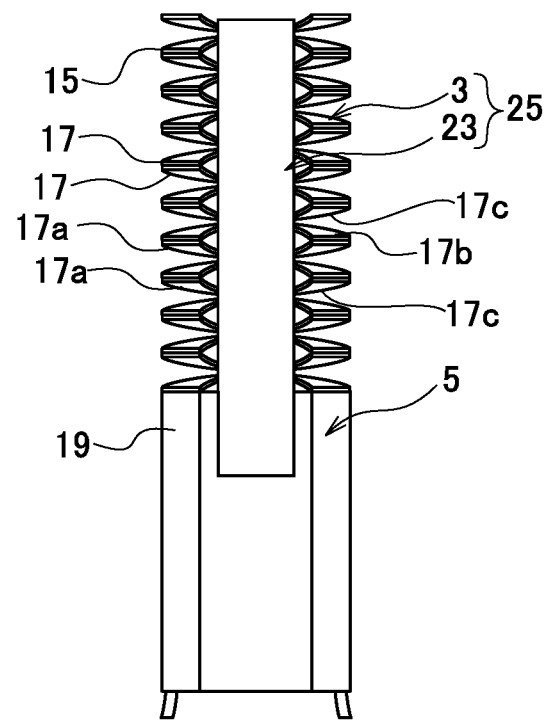
FIG. 27 is a sectional view of the robot forceps of FIG. 25.

FIG. 25 is a perspective view of partly omitted robot forceps using a bending structure according to the embodiment 4 of the present invention, FIG. 26 is a side view of the same, and FIG. 27 is a sectional view of the same. In addition, components in the embodiment 4 corresponding to those in the embodiment 3 are represented with the same numerals to eliminate duplicate explanation.

A bending structure 25 of the present embodiment is what an elastic member 23 is made solid cylindrical. The others are the same components as the embodiment 3.

Namely, the elastic member 23 is formed of elastic material such as rubber into a solid cylinder. With this, the elastic member 23 is configured to have higher rigidity in an axial direction than a main body 15 of a flexible tube 3 and be bendable according to bending of the flexible tube 3.

In addition, in the present embodiment, since the solid cylindrical elastic member 23 is located on an axial center portion of the flexible tube 3, drive wires or the like may be employed instead of a push/pull cable 13 to drive a grasping unit 9.

Figure 28:
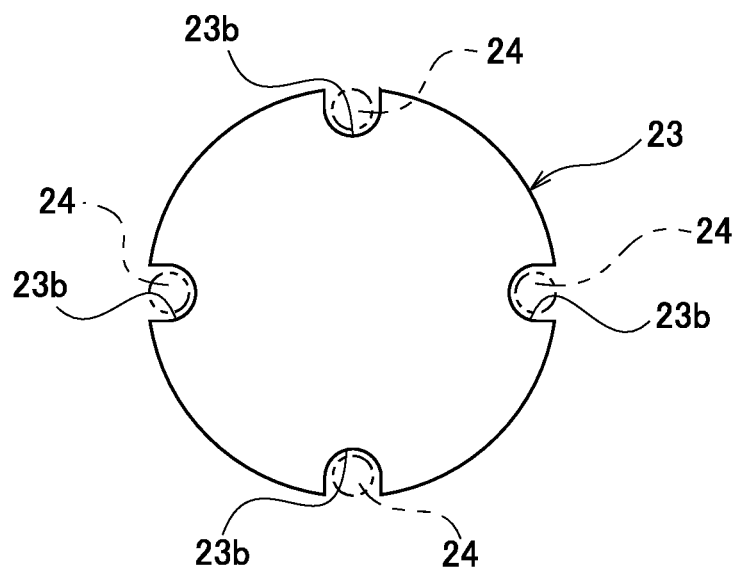
FIG. 28 is a plan view of an elastic member according to a modification of the embodiment 4.
Figure 29:
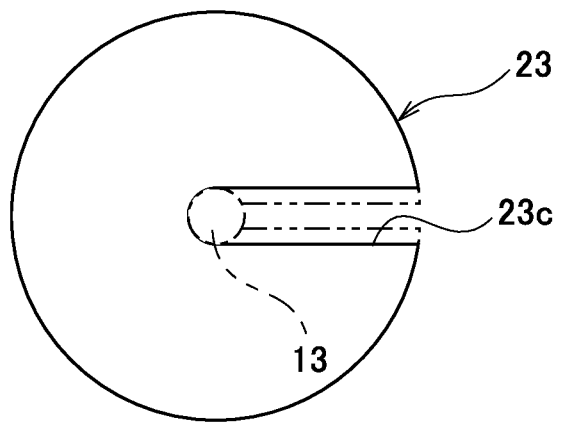
FIG. 29 is a plan view of an elastic member according to another modification of the embodiment 4.

FIG. 28 a plan view illustrating an elastic member 23 according to a modification, and FIG. 29 is a plan view illustrating an elastic member 23 according to another modification.

The modification of FIG. 28 forms groove portions 23b on an outer periphery of the solid cylindrical elastic member 23, the groove portions being recessed in a radial direction. The groove portions 23b are provided along the elastic member 23 in the axial direction, to guide drive wires 24 employed instead of the push/pull cable 13 for driving the grasping unit 9.

It should be noted that the number and the arrangement of the drive wires 24 are appropriately altered according to the structure of the grasping unit 9, and accordingly the number and the arrangement of the groove portions 23b are appropriately altered.

The modification of FIG. 29 provides the solid cylindrical elastic member 23 with a slit 23c being recessed from an outer periphery to the vicinity of an axial center portion in the radial direction. The slit 23c is provided along the elastic member 23 in the axial direction to guide the push/pull cable 13 in the axial center portion of the elastic member 23.

In addition, the slit 23c, as illustrated with a two-dot chain line, may be configured to be slightly narrower than a diameter of the push/pull cable 13 from the outer periphery of the elastic member 23 before the axial center portion and have the same diameter as the push/pull cable 13 at the axial center portion. Further, the slit 23c may be provided so as to pass across the axial center portion of the elastic member 23.

The embodiment 4 and the modifications provide the same effects as the embodiment 3.

Figure 30:
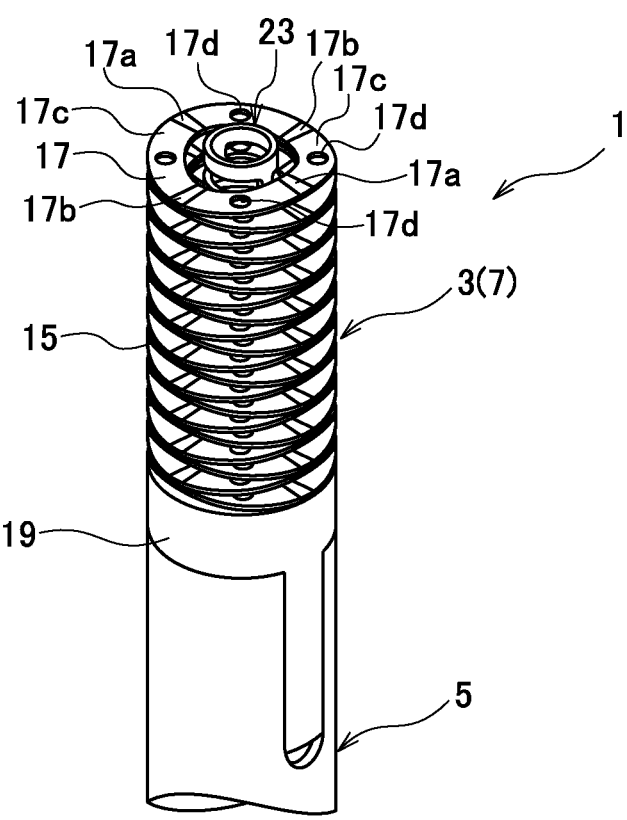
FIG. 30 is a perspective view of partly omitted robot forceps using a bending structure according to an embodiment 5 of the present invention.
Figure 31:
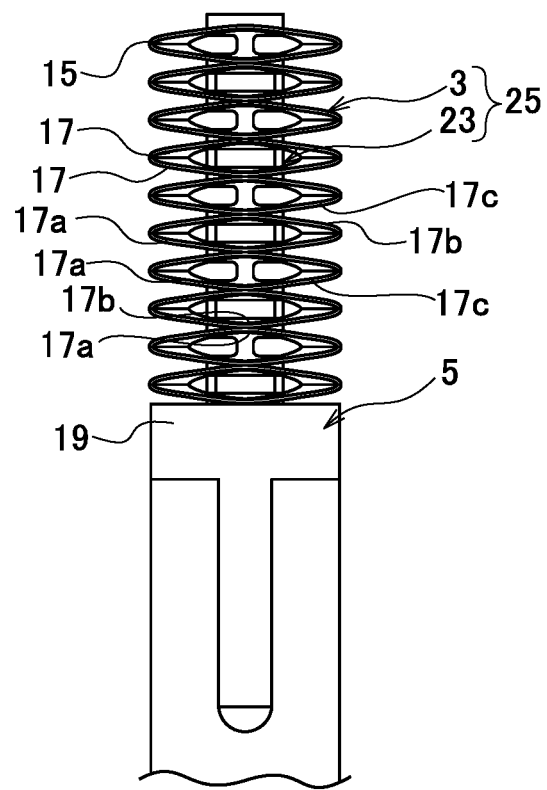
FIG. 31 is a side view of the robot forceps of FIG. 30.
Figure 32:
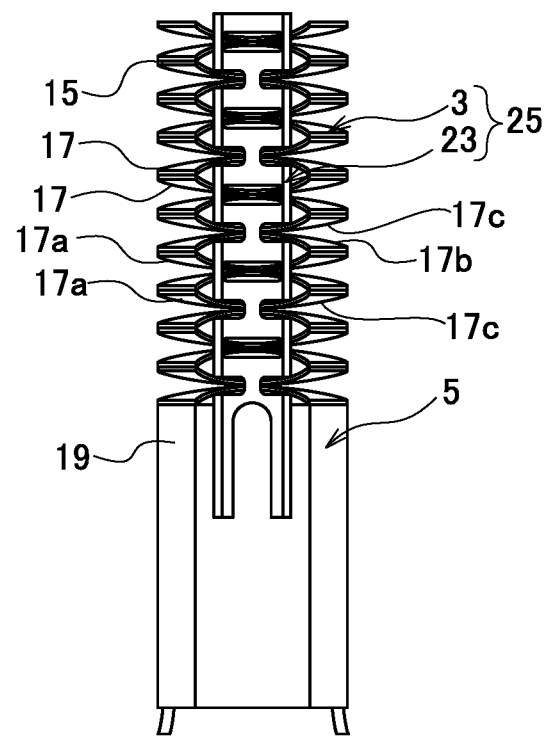
FIG. 32 is a sectional view of the robot forceps of FIG. 30.
Figure 33:
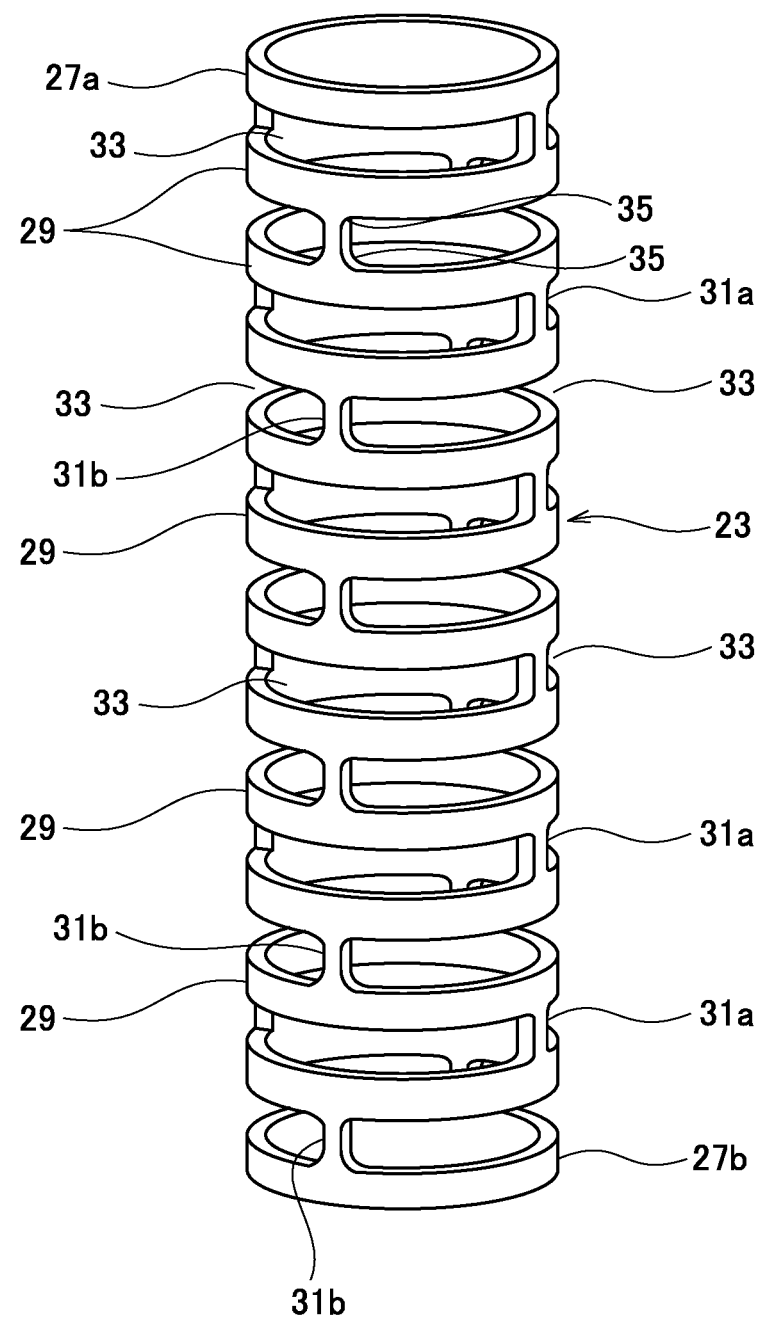
FIG. 33 is a perspective view of an elastic member used for the bending structure of FIG. 30.

FIG. 30 is a perspective view illustrating a bending structure according to the embodiment 5 of the present invention, FIG. 31 is a side view of the same, and FIG. 32 is a sectional view of the same. FIG. 33 is a perspective view illustrating an elastic member of the bending structure of FIG. 30. In addition, components in the embodiment 5 corresponding to those in the embodiment 3 are represented with the same numerals to eliminate duplicate explanation.

A bending structure 25 of the present embodiment is what an elastic member 23 is made into a hollow cylinder. The others are the same components as the embodiment 3.

The elastic member 23 is made of super elastic alloy and comprises end tube portions 27a, 27b, ring portions 29, tube connecting portions 31a, 31b, and tube slits 33. In addition, the super elastic alloy may be NiTi alloy (Nickel-titanium alloy), titanium-base alloy such as gummetal (registered trademark), Cu—Al—Mn alloy (copper-base alloy), Fe—Mn—Al alloy (iron-base alloy) or the like.

The end tube portions 27a, 27b are rings provided at respective end portions. Between the end tube portions 27a, 27b, the ring portions 29 are located.

The ring portions 29 are successively parallelly provided at regular intervals in an axial direction. Spreads in the axial direction of the ring portions 29 are constant according to the embodiment. The spreads in the axial direction of the ring portions 29 may be, however, gradually reduced from a stationary side located on a shaft portion 5 side to a movable side located on a grasping unit 9 side.

The adjacent ring portions 29 are connected by the tube connecting portions 31a, 31b at parts in a circumferential direction. The ring portions 29 at respective ends are connected by the tube connecting portions 31a, 31b to the end tube portions 27a, 27b.

The tube connecting portions 31a, 31b are provided integrally to the ring portions 29 and connects the ring portions 29 being adjacent to each other in the axial direction at two parts in the circumferential direction, the two parts opposing each other in a radial direction.

In each ring portion 29, the tube connecting portions 31a, 31b located on one side (base end side) in the axial direction and the tube connecting portions 31a, 31b located on the other side (front end side) in the axial direction are arranged to be displaced by 180/N degrees in the circumferential direction.

The displacement of the tube connecting portions 31a, 31b means displacement between center lines of the tube connecting portions 31a, 31b (the same shall apply hereinafter). N is an integer equal to or more than 2. According to the present embodiment, N=2 is set and the tube connecting portions 31a, 31b are arranged to be displaced by 90 degrees.

It should be noted that the displacement between the tube connecting portions 31a, 31b may be 60 degrees or the like, but is preferably 90 degrees. This reduces the number of the ring portions 29 required to bend the flexible tube 3 and makes the entire length compact.

Each tube connecting portion 31a, 31b is a rectangular plate extended in the axial direction and has a slight curvature according to the ring portion 29. Widths of the tube connecting portions 31a, 31b in the circumferential direction are constant according to the present embodiment and may be gradually reduced from the stationary side located on the shaft portion 5 side to the movable side located on the grasping unit 9 side.

If the widths of the tube connecting portions 31a, 31b in the circumferential direction are gradually reduced toward the movable side, the spread of the ring portions 29 in the axial direction may be smaller than the maximum width of the connecting tube portion 31a, 31b in the circumferential direction. In this case, the minimum width of the tube connecting portion 31a, 31b in the circumferential direction is preferably set equal to the spread of the ring portions 29 in the axial direction.

Both ends of the tube connecting portions 31a, 31b in the axial direction transition through arc portions 35 to the ring portions 29. Accordingly, the tube connecting portions 31a, 31b and the ring portions 29 are tangentially continued to each other.

In addition, the tube connecting portions 31a, 31b and the ring portions 29 transition to each other with no step on respective inner and outer peripheries in the radial direction of the ring portions 29. The tube connecting portions 31a, 31b may have, however, form to be thicker or thinner than the ring portions 29 to have steps.

The tube connecting portions 31a, 31b bend so that one side of a neutral axis as a boundary in the circumferential direction is compressed and the other side in the circumferential direction is extended, to allow the flexible tube 3 to be bent.

According to the present embodiment, the tube connecting portions 31a, 31b displaced by 90 degrees in the circumferential direction are bent to allow bending in two different orthogonal directions.

On both sides of each tube connecting portion 31a, 31b in the circumferential direction, the tube slits 33 are provided to allow the bending of the flexible tube 3 based on the bending of the tube connecting portions 31a, 31b.

Namely, the tube slits 33 are defined on both sides of the tube connecting portions 31a, 31b in the circumferential direction between the ring portions 29 being adjacent to each other in the axial direction. Each tube slit 33 is a rectangular shape with rounded corners according to the shapes of the ring portions 29 and the tube connecting portions 31a, 31b.

With this structure, the elastic member 23 of the present embodiment has the higher rigidity in the axial direction than the main body 15 of the flexible tube 3 and is configured to be bendable according to the bending of the flexible tube 3.

The embodiment 5, therefore, also provides the same effects as the embodiment 3.

Additionally, according to the embodiment 5, the elastic member 23 made of the super elastic alloy is formed by connecting the ring portions 29 to each other with the tube connecting portions 31a, 31b in the axis direction and is bendable according to the bending of the tube connecting portions 31a, 31b, thereby to conduct size reduction and provide the superior load bearing and bendability. Based on the characteristics, the present embodiment improves the characteristics of the whole bending structure 25.

Further, the elastic member 23, with the structure to connect the ring portions 29 by the tube connecting portions 31a, 31b, is superior in torsional rigidity. Accordingly, the present embodiment improves the torsional rigidity of the bending structure 25.

The invention claimed is:

1. A flexible tube through which drive wires for a medical manipulator are passed in an axial direction and being configured to be bent according to operation of the drive wires, comprising:
   a main body having wave washers stacked in the axial direction and kept a stacked state, the main body being bendable according to expansion and contraction in the axial direction,
   wherein
   each of the wave washers is provided with crests, troughs, inclined portions and through portions, the through portions being configured for passage therethrough of the drive wires, the troughs, the crests and the inclined portions being arranged in a circumferential direction of each of the wave washers, each of the troughs being interposed between circumferentially adjacent crests, each of the inclined portions being interposed between a crest and a trough which are circumferentially adjacent to each other, the through portions being formed on the inclined portions, each of the through portions formed on the inclined portions being entirely within a respective one of the inclined portions, and
   the crests and the troughs of adjacent wave washers are in contact with each other.

2. The flexible tube according to claim 1, wherein
   the crests and troughs being in contact are fixed to each other in the adjacent wave washers.

3. The flexible tube according to claim 1, wherein
   the through portions are insertion holes.

4. A bending structure being provided with the flexible tube according to claim 1, comprising:
   an elastic member arranged in the main body, having higher rigidity in the axial direction than the main body, and being bendable according to the bending of the flexible tube.

5. The bending structure according to claim 4, wherein
   the elastic member is a coiled spring, a solid cylinder, or a hollow cylinder located on an axial center portion of the main body.

6. The flexible tube according to claim 1, wherein
   each through portion is arranged within a width of each of the wave washers.

7. A flexible tube, comprising:
   a bendable main body having wave washers stacked in an axial direction and kept in a stacked state; and
   drive wires passing the main body in an axial direction and configured to be operated upon to bend the main body,
   wherein
   each of the wave washers is provided with crests, troughs, inclined portions and through portions, the through portions being configured for passage therethrough of the drive wires, the troughs, the crests and the inclined portions being arranged in a circumferential direction of each of the wave washers, each of the troughs being interposed between circumferentially adjacent crests, each of the inclined portions being interposed between a crest and a trough which are circumferentially adjacent to each other, the through portions being formed on the inclined portions, each of the through portions formed on the inclined portions being entirely within a respective one of the inclined portions, and
   the crests and the troughs of adjacent wave washers are in contact with each other.

8. The flexible tube according to claim 7, wherein each through portion is arranged within a width of each of the wave washers.

* * * * *